United States Patent [19]

Yamamoto

[11] 4,443,893
[45] Apr. 24, 1984

[54] GOGGLES FOR SKI USE

[75] Inventor: Kenji Yamamoto, Higashi-Osaka, Japan

[73] Assignee: Yamamoto Kogaku Co., Ltd., Osaka, Japan

[21] Appl. No.: 289,094

[22] Filed: Jul. 31, 1981

[30] Foreign Application Priority Data

Aug. 5, 1980 [JP] Japan .................. 55-111574[U]

[51] Int. Cl.³ .............................................. A61F 9/02
[52] U.S. Cl. ........................................ 2/436; 2/171.3
[58] Field of Search ............... 2/436, 437, 435, 171.3, 2/8, 9

[56] References Cited

U.S. PATENT DOCUMENTS

| | | |
|---|---|---|
| 3,825,953 | 7/1974 | Hunter .................................... 2/437 |
| 4,150,443 | 4/1979 | McNeilly ............................... 2/436 |
| 4,238,857 | 12/1980 | Waters ................................... 2/171.3 |
| 4,309,774 | 1/1982 | Guzowski ........................ 2/171.3 X |

Primary Examiner—Peter P. Nerbun
Attorney, Agent, or Firm—Armstrong, Nikaido, Marmelstein & Kubovcik

[57] ABSTRACT

Ski goggles are composed of goggle frame, goggle lens and rubber band. Vent holes are formed, respectively, in the top peripheral wall portion and the bottom peripheral wall portion of the goggle frame. A permeable coating material is engaged to cover the vent holes. A mounting stand, which serves as duct, is engaged in the central portion of the top peripheral wall portion of the goggle frame. A ventilating fan and a small-size motor for driving the fan are mounted on the mounting stand. The ventilating fan is adapted to compulsorily ventilate the air within the inner space formed between the goggle lens and the face, and is accommodated within the mounting stand. The motor can be turned on or off by a power supply switch. The number of the revolutions can be controlled by the controlling circuit or can be controlled by a controlling circuit or in accordance with the humidity of the inner space.

3 Claims, 10 Drawing Figures

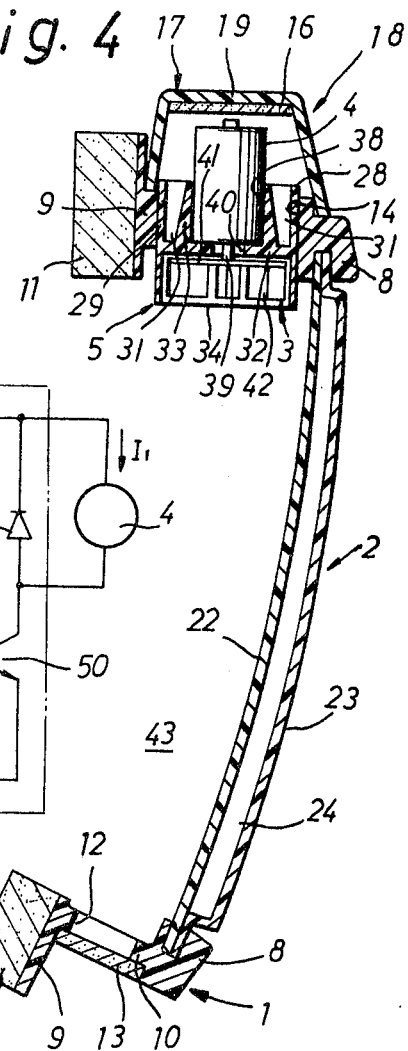
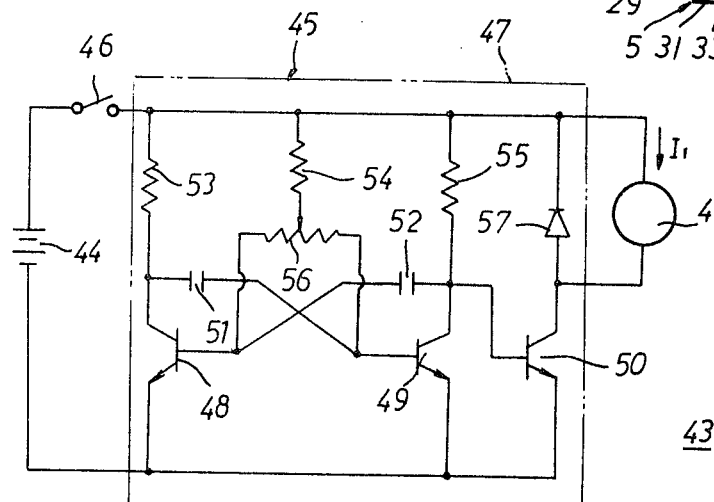
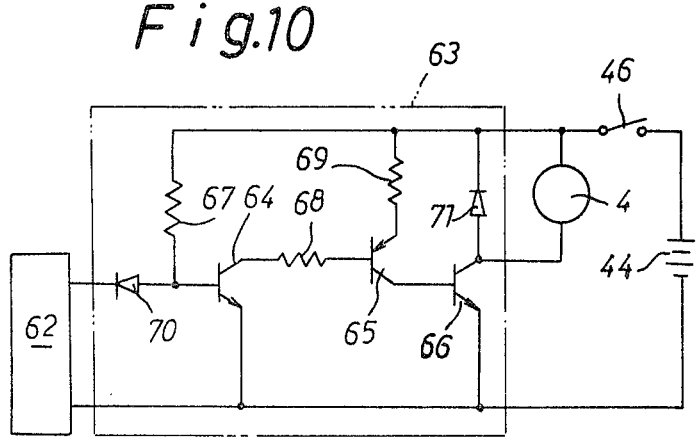

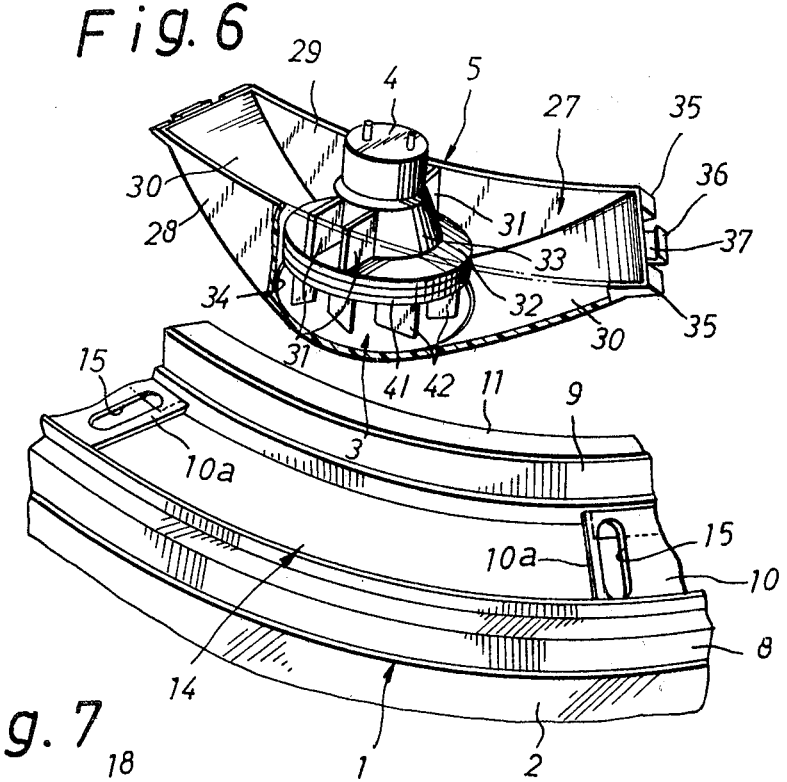
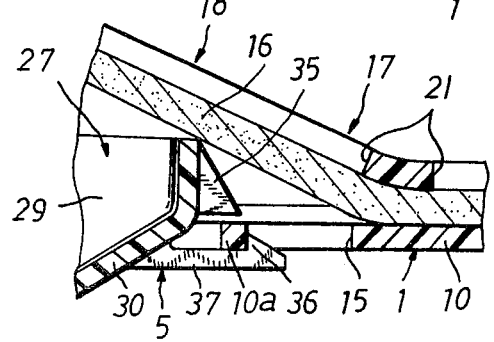
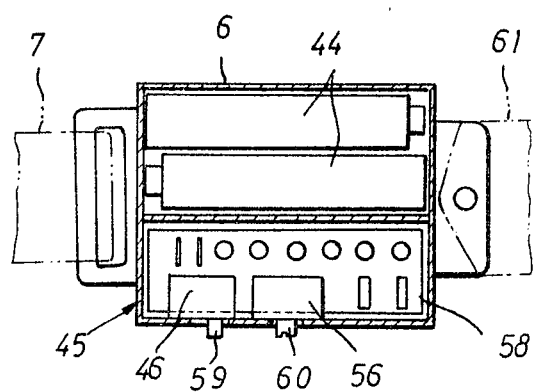

GOGGLES FOR SKI USE

BACKGROUND OF THE INVENTION

The present invention relates to goggles for ski use. The present invention is adapted to forceably ventilate the air located in the inner space by means of a ventilating fan to prevent the goggle lens from being fogged.

Since the ski goggles are used at extremely cold temperatures, the goggle lens becomes fogged due to the bodily temperatures, perspiration, etc. of the skier during the use of the goggles, particularly when the skier stops his skiing, with the result that accidents are caused due to the deteriorated visual field. A measure to be taken to prevent the lens from being fogged under such a case is extremely effective if the air ventilation of the inner space to be formed within the goggle frame is performed between the lens and the face thereby to forceably exchange the high-humidity warm air located of the inner space for the low-humidity and -temperature of the open air. Thus, ski goggles are proposed, which are provided, at and middle portion of the goggle frame, with a ventilating fan and a small-sized motor for driving it to introduce the open air into the inner space through the rotation of the ventilating fan.

In prior art arrangements, a mounting portion was integrally formed in the upper and middle position of the goggle frame. A ventilating fan and a motor were mounted on this mounting portion. Accordingly, it was difficult to manufacture the goggle frame and a hard material was required to be used as the goggle frame. Namely, the goggle frame, which was normally made of material such as synthetic resin or the like, was integrally molded. However, when the mounting portion was integrally provided, the shape of the goggle frame became extremely complicated so that it was difficult to manufacture the goggle frame. Also, although a relatively soft and flexible material was used for the goggle frame so that unpleasant feelings were not accompanied when the goggles were put on the face of the user, the entire goggle frame became disadvantageously hard, since a material to be usable was limited to a relatively hard one. This was because the shape retaining property of the mounting portion was demanded to firmly secure the ventilating fan and the motor when the mounting portion was integrally formed. In addition, the operation became complicated, since the ventilating fan and the rotor were required to be individually mounted on the goggle frame in the assembling operation. Also, as the ventilating fan projected onto the inner space side from the goggle frame, safety was not ensured. The user was injured due to accidental contact against the ventilating fan during rotation.

SUMMARY OF THE INVENTION

A first object of the present invention is to provide a pair of ski goggles wherein the goggle frame and a mounting stand on which the ventilating fan and the motor are mounted are separately constructed.

A second object of the present invention is to provide a pair of ski goggles, wherein a material to be used for the goggle frame and the mounting frame is optically selected, and the mounting operation of the ventilating fan and the motor can be reliably performed without any effect on the goggle frame flexibility.

A third object of the present invention is to provide a pair of ski goggles wherein the ventilating fan and the motor are combined with the mounting stand as a unit to improve the operational efficiency during the assembling operation.

A fourth object of the present invention is to provide a pair of ski goggles superior in safety wherein the ventilating fan is disposed within the mounting stand.

Other features and advantages of the present invention will be apparent from the following description taken in connection with the accompanying drawings.

BRIEF DESCRIPTION OF THE DRAWINGS

The drawings show ideal embodiments of the present invention.

FIG. 4 is an enlarged cross-sectional view of the essential portions.

FIG. 6 is a break-away perspective view of a condition where the mounting stand is disengaged from the goggle frame.

FIG. 7 is an enlarged view of a portion of FIG. 3.

FIG. 8 is a cross-sectional view of a control box portion.

FIG. 9 is a circuit diagram of a control apparatus.

FIG. 10 is a circuit diagram showing another embodiment of the control apparatus.

DETAILED DESCRIPTION OF THE INVENTION

Figure 1:
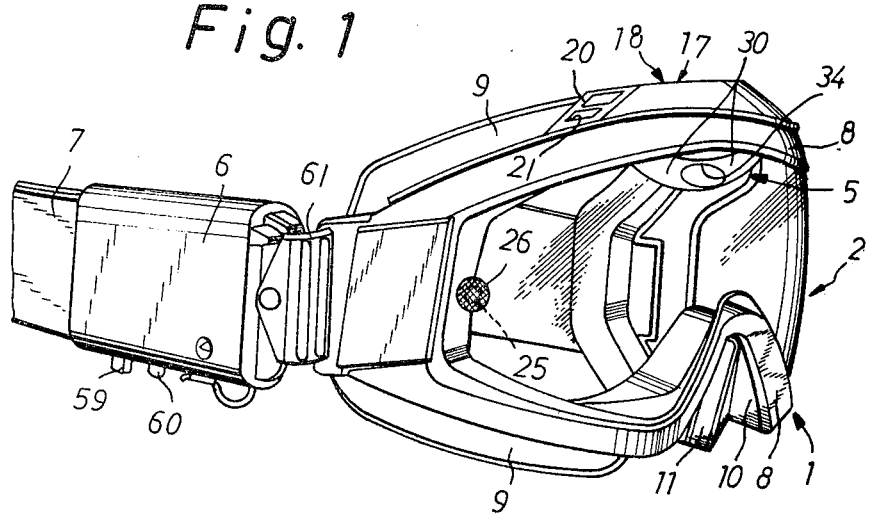
FIG. 1 is a perspective view of the entire goggles for ski use.
Figure 2:
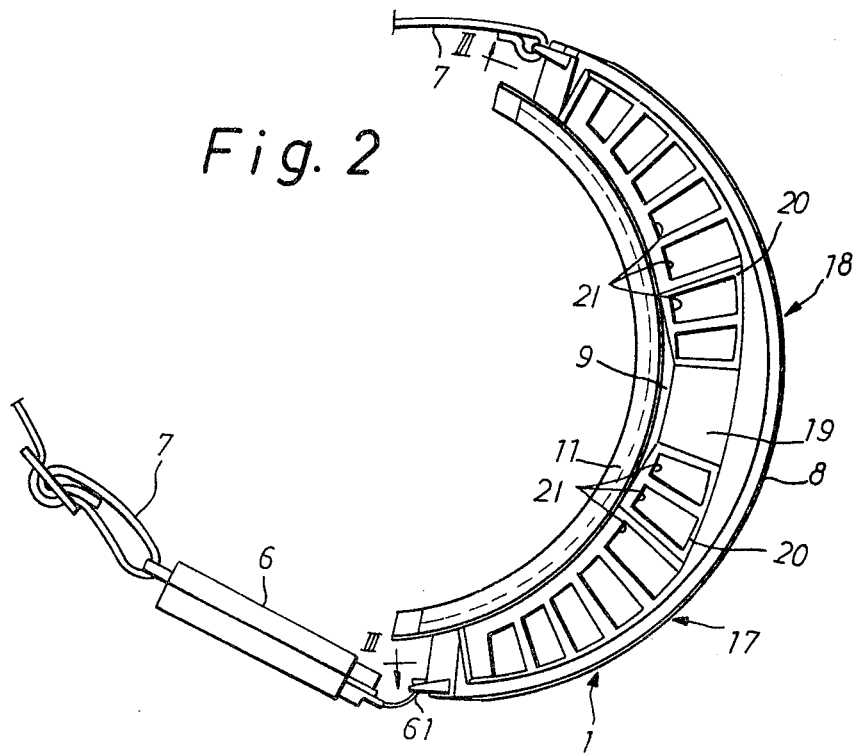
FIG. 2 is the same plan view thereof.

FIG. 1 and FIG. 2 show the ideal embodiment of the ski goggles in accordance with the present invention. The ski goggles are composed of goggle frame (1), goggle lens (2) engaged with the goggle frame (1), ventilating fan (3), motor (4), mounting stand (5) engaged with the goggle frame (1), control box (6) disposed halfway, rubber band (7) coupled to the goggle frame (1), etc.

Figure 3:
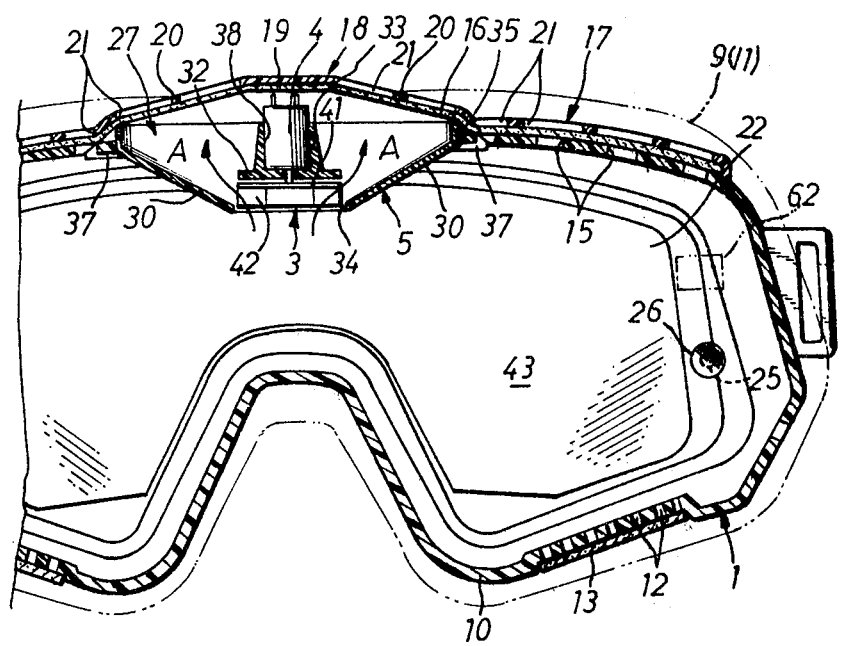
FIG. 3 is a perspective view taken along a line III—III of FIG. 2.
Figure 5:
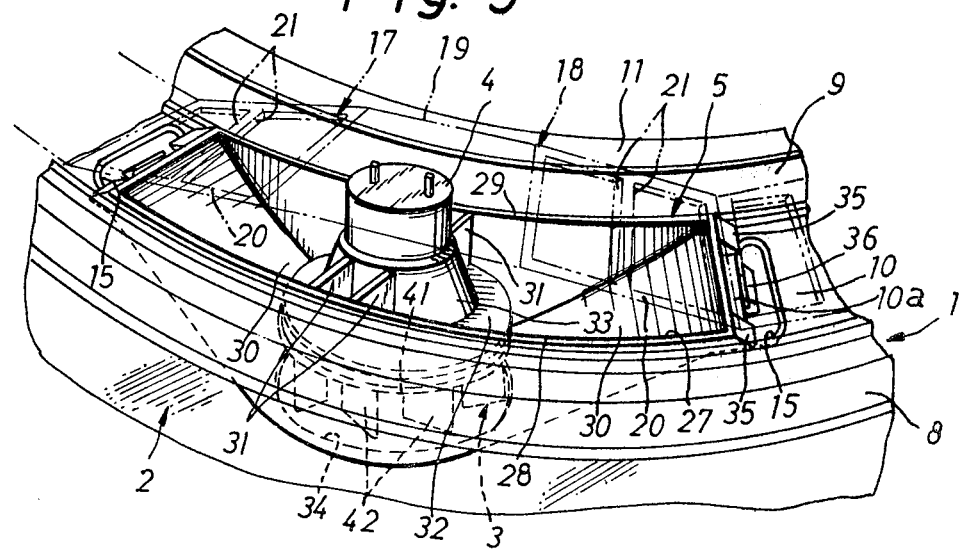
FIG. 5 is a perspective view of a mounting stand portion from which the cover body, etc. are disengaged.

The goggle frame (1) is composed of a soft material such as vinyl, rubber or the like. As shown in FIG. 3 and FIG. 4, the goggle frame (1) is composed of a lens engagement edge (8), a face contact washer (9), peripheral wall portion (10) coupling the lens engagement edge to the face contact washer. The goggle lens (2) is detachably engaged with the lens engagement edge (8). An adherent material (11) such as sponge, montplane or other cushion-like material is cemented on the face contact washer (9). The goggle frame (1) is adapted to adhere against the face across the entire periphery through the adherent material (11). A plurality of vent holes (12) are formed on the right and left sides of the lower-side peripheral edge portion (10). A permeable strap-shaped coating material (13) composed of continuous blister such as polyurethane foam, sponge or the like are cemented, on the outer face side, in closed shape to cover a vent hole (12) thereby to prevent snow, dust or the like from entering from the vent hole (12). Also, a circular mounting opening (14) is formed in the central portion of the upper side peripheral wall portion (10) and a plurality of vent openings (15) and formed on the both sides. And a permeable strap-shaped coating material (16) made of the continuous blister body or the like similar to the above blister is provided on the upper face side of the upper side of the peripheral wall portion (10) to cover the mounting opening (14) and the ventilation opening (15) and a cover body (17) is detachably engaged or pasted to cover the coating material (16). The cover body (17), which is made of a soft material such as vinyl, rubber or the like, is provided, on its central portion, with a raised portion (18) corresponding to the mounting opening (14). The raised portion (18), which is composed of a central flat portion (19) and right, left slant face portions (20). A plurality of vent holes (21) are formed on the both sides of the raised portion (18) of the slant face portion (20) and the cover body (17).

As shown in FIG. 4, the goggle lens (2) is provided with inner and outer lens plates (22), (23) each being of transparent colored plastic and given inner space (24) is formed between the inner and outer lens plates (22), (23). A pin-hole-shaped vent hole (25) which is communicated with the inner space (24) is formed in the inner lens plate (22) and water rejecting filter (26) is pasted corresponding to the vent hole (25). This filter (26) allows only the air to flow into the inner space (24) and prevents the water from penetrating into the space (24).

The mounting stand (5) is made of a synthetic resin material or the like, which is harder than the goggle frame (1) and is provided, on its top portion, with an opening portion (27) and on its bottom portion, with a projection. The mounting stand (5) is composed of front and rear walls (28), (29), a pair of right and left curved lower walls (30) coupling the wall (28) to the wall (29), and a conical stand portion (33) secured, through a pair of plate-shaped portions (31), to each of the central portions of the front and rear walls (28), (29) and provided, on its bottom face, with a disc portion (32). A circular ventilating opening (34) located in the bottom portion of the mounting stand (5) is formed between the lower walls (30) and the interior of the mounting stand (5) forms a duct. A pair of triangular upper pawls (35), are located in the front and rear portions at each end of mounting stand (5), and an overhang portion (37) is located between the upper pawls (35) and is provided, at its tip end portion, with a triangular lower pawl (36) projecting outwardly. The mounting stand (5) is inserted from below into the mounting opening (14) of the goggle frame (1) and a strap-shaped portion (10a) between the mounting opening (14) of the upper peripheral portion (10) of the goggle frame (1) and the right, left vent holes (15) adjacent to the mounting opening is inserted, through elastic deformation, between the upper pawl (35), the lower pawl (36) and the overhang portion (37), whereby mounting stand (5) is detachably engaged as a downward projection within the upper peripheral portion (10) of the goggle frame (1). It is to be noted that the mounting stand (5) is coated, on its top side, with a coating material (16) and by the raised portion (18) of the cover body (17). An equipment hole (38), which is open in a vertical direction, is formed in a conical stand portion (33). A cylindrical small motor (4) is detachably engaged, as an upward projection, into the equipment hole (38). The output shaft (39) of the motor (4) is downwardly projected through the small hole (40) of the disc portion (32). A ventilating fan (3) is fixedly disposed, in the under end of the output shaft (39), corresponding to the ventilating opening (34) so that it may be accommodated into the mounting stand (5). As the fan, a turbo centrifugal fan is used to provide maximum air pressure with revolution number and size which have been set, respectively, to a given value. The fan (3) is composed of a circular base (41) and a plurality of blades (42) secured to the base (41). The motor (4) is driven to externally discharge the air, which is located within the inner space (43) formed between the goggle lens (2) and the face. As the fan (3), an axial fan may be used.

A power supply (44) such as battery or the like and a controlling device (45) for controlling the motor (4) are accommodated, as shown in FIG. 8, within a controlling box (6). As shown in FIG. 9, the controlling device (45) is composed of a power supply switch (46), an oscillation circuit (47) or the like. The oscillation circuit (47), which is composed of transistors (48), (49), (50), capacitors (51), (52), resistors (53), (54), (55), a variable resistor (56), a diode (57), etc., is constructed as an unstable multivibrator. Each element of the power supply switch (46) and the oscillation circuit (47) are disposed on a print substrate (58). Also, the power supply switch (46) and the variable resistor (56) can be operated, respectively, by operating units (59), (60), which are downwardly projected from the controlling box (6). The power supply switch (46) is not restricted to a slide type although the slide type is used.

One end of the controlling box (6) is coupled to one end portion of the goggle frame (1) through a coupling piece (61). The coupling piece (61), which is made of a soft material such as vinyl, rubber, etc., is flexible. One end side of a rubber band (7) is coupled for free adjustment length to the other end of the controlling box (6) and the other end side thereof (7) is coupled to one end portion of the goggle frame (1). When the controlling box (6) is provided between one end portion of the rubber band (7) and the one end portion of the goggle frame (1), the controlling box (6) does not become bulky. The controlling box (6) may be provided on the other portion of the goggles or may be provided as a separate unit so that the skier may carry on his body.

The function of such construction will be described hereinafter. When the skier has the goggles on in the cold temperatures, dry cold open air naturally flows through the vent hole (21) of the cover body (17), and the vent holes (12), (15), etc. of the coating materials (13), (16) and the goggle frame (1), during the skiing operation, into the inner space (43) formed between the goggle lens (2) and the face of the skier, and correspondingly the air within the inner space (43) is also externally discharged, thus making it difficult to fog the goggle lens (2). Since the open air flows no more into the inner space (43) when the skiing stops, the air within the inner space (43) becomes warm and moist due to the bodily temperatures and the perspring function of the skier, with the result that the steam becomes saturated. On the other hand, since the goggle lens (2) is cooled with the open air, water drops are formed on the inner face of the inner lens plate (22) of the goggle lens (2) due to the condensation of the steam contained in the air within the inner space (43), thus resulting in fogging of the lens. In this case, the power supply switch (46) of the controlling box (6) is turned on to operate the motor (4) to drive the fan (3).

Turning on the power supply switch (46) the oscillation circuit (47) to generate square pulses. The pulse signals are applied to the motor (4) so that the motor (4) starts to rotate with the number of the revolutions corresponding to the pulse signals. Namely, assume that a transistor (48) is ON and a transistor (49) is OFF in the oscillation circuit (47), and a transistor (50) is turned on to flow a current $I_1$ to the motor (4). At this time, the electric charge of a capacitor (51) is being discharged through resistors (53), (54), (56). As the discharging operation is performed after some lapse of time, the transistor (49) is turned on. Since during the OFF period, a capacitor (52) is kept charged to approximate power-supply voltage through a resistor (55), the charging voltage is applied upon the transistor 48 to turn off the transistor (48) when the transistor (49) is turned on. Also, simultaneously the electric charge of the capacitor (52) is discharged through resistors (55), (54), (56). After some lapse of time, the transistor (48) is switched from OFF to ON thereby turning off the transistor (49). When the transistor (49) is turned on, the transistor (50) is turned off to cut off the current $I_1$ of the motor (4). As described hereinabove, the oscillation circuit (47) repeats the ON . OFF operations of the transistors (48), (49), (50). The ON . OFF period can be optionally controlled by varation of the time constant through the operation of the variable resistor (56). Accordingly, the motor (4) is driven by a pulse controlling system so that the number of the revolutions can be optionally increased or decreased, and the power loss can be minimized during the increasing or decreasing operation.

Upon rotation the fan (3), the moist air within the inner space (43) is sucked upwardly, as shown with an arrow of FIG. 3, through the ventilating opening (34) of the mounting stand (5). The sucked air is introduced to an opening portion (27) through the duct construction within the mounting stand (5). And the air introduced into the opening portion (27) is externally discharged through the coating material (16) mainly through the vent hole (21) of the raised portion (18) of the cover body (17). Since the pressure within the inner space (43) becomes negative due to this discharging operation, dry, cold open air flows into the inner space (43) through the vent holes (21) of the cover body (17), the vent hole (12), (15) of the coating materials (13), (16) and the goggle frame (1). Since the air located within the inner space (43) is forceably replaced by the dry, cold open air through the driving operation of the fan (3) in this manner, the fogged condition of the inner lens plate (22) is removed. Also, the air is moved within the inner space (43) due to the driving operation of the fan (3). This is also effective to remove the fogged condition. Since the open air is uniformly penetrated from the vent holes (12), (15) of the goggle frame (1) into the inner space (43) due to the driving operation of the fan (3), the air flow is locally concentrated in spite of the forced ventilation so that the eyelashes are not blown violently or the eyes irritated. Accordingly, no discomfort is caused to the skier. Turning on the power supply switch (46) immediately before skiing stops prevents the goggle lens (2) from being fogged. In a case where the skier uses goggles together with glasses for correcting vision, moist and warm air comes into contact with the lens of the glasses, which have been exposed cold open air flowing into the inner space (43), when the skiing operation has stopped, to cause the fogged condition. However, this fogged condition can be removed or be prevented, due to the driving opertion of the fan (3).

Since the goggle lens (2) is composed of inner and outer lens (22), (23) to form the inner space (24), as an adiabatic layer, between the lens plates (22), (23), the goggle lens (2) is hard to fog even if the difference between the open air temperature and the air temperature within the inner space (43) between the goggle lens (2) and the face is large. Accordingly, a fan (3), whose ventilation amount is relatively small, can be used.

Since the goggle frame (1) and the mounting stand (5) are separately made in construction, and the fan (3) and the motor (4) are mounted on the mounting stand (5), all that is required is to in advance put together the fan (3) and the motor (4) on the mounting stand (5) to engage it into the mounting opening (14) of the goggle frame (1). The mounting stand (5), the fan (3) and the motor (4) can be handled as the unit to considerably improve the efficiency of the assembling operation. Also, since the goggle frame (1) and the mounting stand (5) are separate, a soft material can be selected for the goggle frame (1) and a hard material can be selected for the mounting stand (5). The fan (3) and the motor (4) can be firmly mounted on the mounting stand (5) without any damage of the flexibility of the goggle frame (1). Only a mounting opening (14) or the like is required to be formed in the goggle frame (1) for the engagement. The goggle frame (1) can be simplified in construction and is easier to manufacture. Since the fan (3) is accommodated within the mounting stand (5), problems such as accidental contact against rotating fan (3) are avoided, thus improving the safety.

In FIG. 10, the humidity of the inner space (43) of the goggles is adapted to be detected to control the motor (4). It is composed of a humidity sensor (62) and a controlling circuit (63). The humidity sensor (62) detects the humidity within the inner space (43) and is pasted on the inner face side of the inner lens plate (22) in a position above the filter (26) as shown with a broken line in FIG. 3. The humidity sensor (62) wherein the electric resistance becomes larger through detection of the humidity rise is used. However, it is needless to say that the humidity sensor is not restricted to the above description. The controlling circuit (63) is composed of transistors (64), (65), (66), resistors (67), (68), (69), diodes (70), (71), etc. and is adapted to automatically operate the motor (4) when the inner space (43) is at a given humidity or higher. In this case, the power supply switch is kept on when the goggles are used in the ski fields. Since the electric resistance of the humidity sensor (62) is small when the humidity of the inner space (43) is low at this time, the current flows through the resistor (67), the diode (70) and the humidity sensor (62), but the transistor (64) is not turned on, with the result that the motor (4) remains in its inoperative condition. When a condition is reached where the humidity of the inner space (43) rises to when fogging will occur or to a condition close to the above condition, the electric resistance of the humidity sensor (62) rises to turn on the transistor (64). As a result, the transistors (65), (66) Darlington-connected are turned on to energize the motor (4) to automatically rotate so that forced ventilation will be performed, in the same manner as described hereinabove, by a fan (3).

In this embodiment, a ventilating system which operates through discharging operation has been described. The operation can be performed likewise even in an air intake system or air intake-and-outlet switching system. Also, the controlling system of the motor (4) is not restricted to the pulse controlling system and the ON . OFF controlling system.

What is claimed is:
1. A sport goggle comprising:
 a frame of relatively flexible substantially impervious material having an inner edge adapted to contact the face of the wearer and an outer edge in which a lens is mounted, said frame being formed with a plurality of vent holes in its periphery and an open- ing in its upper portion, said frame and lens forming an inner space about said wearer's face;

a mounting stand of relatively rigid material formed with a ventilating opening in its lower portion and an outwardly flared opening in its upper portion, said mounting stand being detachably positioned with its open upper portion in said opening of said frame and projecting into said inner space to form a duct between said inner space and said opening of said frame and a fan disposed within said mounting stand adjacent to said ventilating opening, whereby operation of said fan will forceably withdraw air from said inner space through said ventilating opening and said duct and thereby cause fresh air to be drawn into said inner space through said vent holes.

2. A sport goggle as claimed in claim 1 further comprising means for manually initiating operation of said fan and for controlling the speed of said fan.

3. A sport goggle as claimed in claim 1 further comprising humidity sensing means positioned in said inner space, and means responsive to said humidity sensing means for causing operation of said fan when the humidity within said inner space is high.

* * * * *